United States Patent [19]
Klainer et al.

[11] Patent Number: 5,253,037
[45] Date of Patent: Oct. 12, 1993

[54] OPTIMAL LENGTH FOR REFRACTIVE INDEX SENSORS

[75] Inventors: Stanley M. Klainer; Devinder P. S. Saini, both of Henderson, Nev.

[73] Assignee: FCI-FiberChem, Inc., Las Vegas, Nev.

[21] Appl. No.: 925,560

[22] Filed: Aug. 4, 1992

[51] Int. Cl.⁵ .................... G01N 21/41; G02B 6/16
[52] U.S. Cl. ..................... 356/133; 385/12; 385/123
[58] Field of Search .............. 356/128, 133; 385/12, 385/123, 126

[56] References Cited

U.S. PATENT DOCUMENTS

| | | | |
|---|---|---|---|
| 4,929,049 | 5/1990 | Le Goullon et al. | 385/12 |
| 5,026,139 | 6/1991 | Klainer et al. | 356/133 |
| 5,165,005 | 11/1992 | Klainer et al. | 356/128 |

Primary Examiner—F. L. Evans
Attorney, Agent, or Firm—Henry P. Sartorio

[57] ABSTRACT

In a refractive index type optical sensor having a thin film metal clad on a waveguide to control leakage of light as a function of refractive index, light leakage occurs in the region where a discontinuity in refractive index occurs. A discontinuous clad with short, closely spaced segments maximizes light leakage and sensitivity over the length of the sensing region. Multiple sensing regions can be formed on a single waveguide.

20 Claims, 3 Drawing Sheets

OPTIMAL LENGTH FOR REFRACTIVE INDEX SENSORS

BACKGROUND OF THE INVENTION

The invention relates generally to optical sensors and more particularly to refractive index waveguide sensors.

U.S. Pat. Nos. 4,929,049 and 5,026,139 and U.S. application Ser. No. 07/646,148, now U.S. Pat. No. 5,165,005, disclose optical sensors with thin film metal clads on an optical fiber or other waveguide structure which operate on the basis of refractive index. The clad is designed so that light leakage through the metal clad is a function of the refractive index of the surrounding medium, which varies with the presence of a target species. The metal clads may be made of adjacent segments of different metals. The metal clads can be selected with great specificity to a particular analyte. Presently these optical sensors are made of arbitrary length, typically one inch. It would be desirable to optimize the sensor length to increase sensitivity and to make the sensor as compact as possible for certain applications.

U.S. Pat. No. 4,913,519 describes an ice sensor which has a segmented clad with gaps formed on a fiber. The presence of air, water or ice in the gaps is determined from resulting changes in the transmission properties of the fiber caused by the change in refractive index.

U.S. Pat. No. 5,109,442 is directed to waterproofing a fiber optic sensor by applying hydrophobic polymers. A patterned polymer clad may be formed over the metal clad on a fiber.

SUMMARY OF THE INVENTION

Accordingly it is an object of the invention to optimize the length of a refractive index based optical sensor.

It is also an object of the invention to increase light leakage over the entire length of the sensing region.

It is another object of the invention to increase sensor sensitivity.

The invention provides a metal clad configuration for a refractive index waveguide sensor which is based on the point of leakage of light from the optical waveguide. Since the light leakage occurs at an index step, the metal clad region of the waveguide can be made very short. On a longer waveguide, a patterned clad which introduces many index discontinuities is used. The clad pattern can be regular or irregular.

DETAILED DESCRIPTION OF THE PREFERRED EMBODIMENTS

The refractive index sensors of the invention are formed in accordance with the principles of U.S. Pat. Nos. 4,929,049 and 5,026,139 and U.S. patent application Ser. No. 07/646,148, now U.S. Pat. No. 5,165,005 which are herein incorporated by reference. A thin film metal clad is formed on a fiber optic or other waveguide. The thin film metal clad controls light leakage from the waveguide as a function of the refractive index of the surrounding medium. The thin film metal clad may be species specific.

Figure 1:
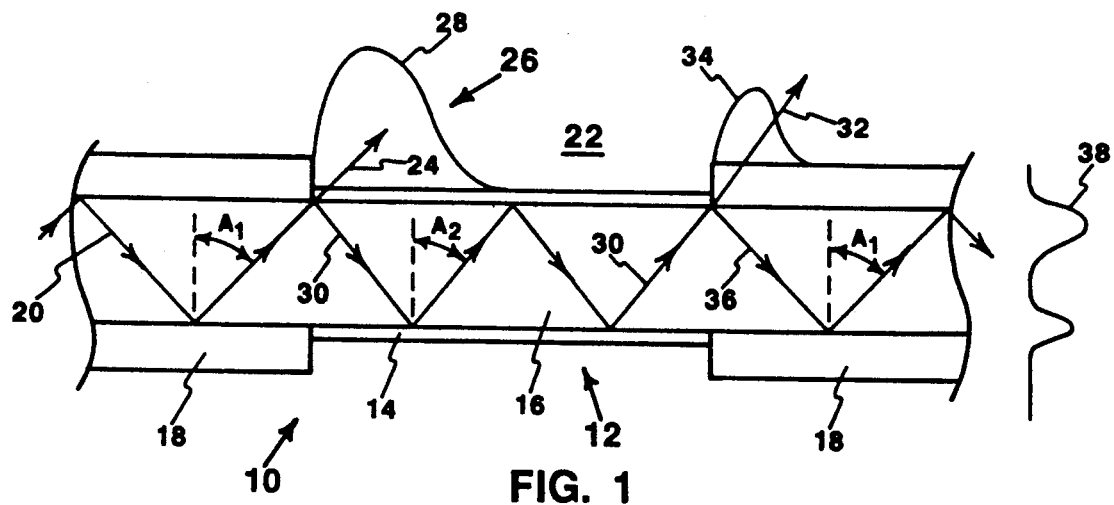
FIG. 1 is a cross-sectional view of a fiber optic refractive index sensor.

The principles of operation of a thin film metal clad refractive index sensor are illustrated in FIG. 1. A fiber optic sensor 10 has a sensor region 12 with a thin film metal clad 14 formed on the core 16 of a multi-mode optical fiber. In region 12, the conventional clad 18 of the optical fiber has been removed prior to formation of the metal clad 14. A light beam 20 propagates down core 16 by total internal reflection at the coreclad interface. The critical angle A for total internal reflection is determined by the ratio of the refractive index of the clad to the core: $\sin A = N_{Clad}/N_{Core}$ where A is measured from the normal to the interface. All rays incident at angles greater than A will be totally internally reflected. The index of the clad must be less than the index of the core for total internal reflection to occur. The numerical aperture NA is related to the critical angle A, and determines which modes propagate in the fiber.

In the regions of the optical fiber where the core 16 is covered by the conventional clad 18, the critical angle is $A_1$ and numerical aperture is $NA_1$ so that all rays incident on the interface at angles greater than $A_1$ will be totally internally reflected and propagate down the fiber core 16. The light beam 20 will be input into the fiber so that substantially all the light is incident at angles of $A_1$ or greater. The modes that propagate are determined by $NA_1$. When the rays of light beam 20 reach the sensor region 12, a different condition exists. The index (N*) of the "clad" in region 12 is a composite of the index of the metal clad 14 and the index of the surrounding medium 22. This index will not be a constant but will be modulated by changes in the surrounding medium, e.g., by the presence of varying concentrations of the species of interest. However, the value of N* will generally differ from the index of clad 18, so that a different critical angle $A_2$ and different numerical aperture $NA_2$ will exist in region 12. The mismatch in numerical apertures $NA_1$ and $NA_2$ causes some modes which are totally internally reflected by clad 18 to not be totally internally reflected by clad 14 and these modes, represented by ray 24, will leak from the sensor 10. Thus, the light leakage will occur in an initial region 26 near the junction of clads 14 and 18. This region will have a length dependent on the width and divergence of beam 20 which determines the spread of the beam when a ray first is incident on clad 14. This light leakage is represented by intensity profile 28. For the remainder of the length of region 12, the remaining portion 30 of incident beam 20 is in modes accepted by numerical aperture $NA_2$ and thus satisfies the condition for total internal reflection. Thus, there is no further leakage of light and the remainder of region 12 is essentially nonfunctional. Therefore, the optimal length of region 12 is substantially the length of region 26 where the leakage shown in profile 28 occurs.

Similarly when the beam 30 propagating in region 12 encounters another numerical aperture mismatch when beam 30 reaches clad 18 at the distal end of region 30 from region 26, some modes of beam 30 will leak from the core, as represented by ray 32, producing a secondary leakage intensity profile 34. The remainder 36 of the light beam will continue to propagate along core 16, forming an output beam which generally has a ring profile shown as intensity profile 38.

Thus, light leakage from the fiber optic sensor occurs primarily at index discontinuities in the clad. Many modes are present in the beam and the numerical aperture of the fiber accepts only particular modes; therefore, when the numerical aperture changes, not all modes are accepted. The rejected modes leak from the fiber. This leakage occurs when the beam first encounters the index (or numerical aperture) mismatch. The modes that are accepted will continue to propagate until another mismatch condition is encountered, where other modes may be rejected.

Therefore, the optimal length for a refractive index sensor is the length of the clad along which the propagating beam first encounters a change in refractive index.

The foregoing principles can be utilized to increase the sensitivity of a refractive index waveguide sensor by designing the sensor with clad segments of optimum length. As shown with reference to FIG. 1, a long continuous clad is not optimal since light leakage occurs only in the region immediately following a discontinuity in refractive index. Thus, the clad region can be shortened to its optimal length. Alternatively, to increase light leakage (and sensitivity) further index discontinuities can be formed along the length of the sensor.

Figure 2:
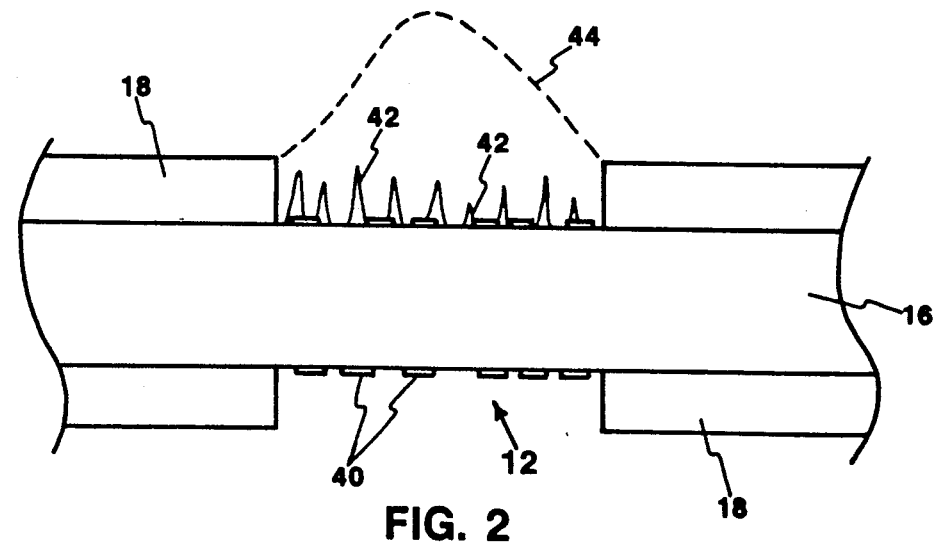
FIG. 2 is a cross-sectional view of a refractive index sensor with irregular clad.

As shown in FIG. 2, a sensor region 12 is formed where conventional clad 18 has been removed from fiber optic core 16. Sensor region 12 is longer than the optimal length for a single continuous clad. However, instead of a single continuous clad, a discontinuous clad 40 is applied in region 12. Clad 40 is made of materials of the type used in refractive index sensors, but is patterned to have numerous closely spaced index discontinuities. The clad 40 may have a regular or irregular pattern. The clad 40 may take the form of stripes separated by air gaps, or random islands or any other discontinuous geometry. Each segment of clad 40 introduces two discontinuities, one at each end.

If the spacings between the discontinuities in clad 40 are close to optimal for light leakage, then the amount of light leakage in region 12 will be maximized, giving maximum sensitivity to the sensor. Each discontinuity produces light leakage represented by intensity profiles 42. If the intensity profiles 42 are sufficiently close, or overlap, the intensity profiles will combine to form an aggregate intensity profile 44. A sensor designed in this manner has been optimized for light leakage and sensitivity over a sensing region of desired length.

Figure 3:
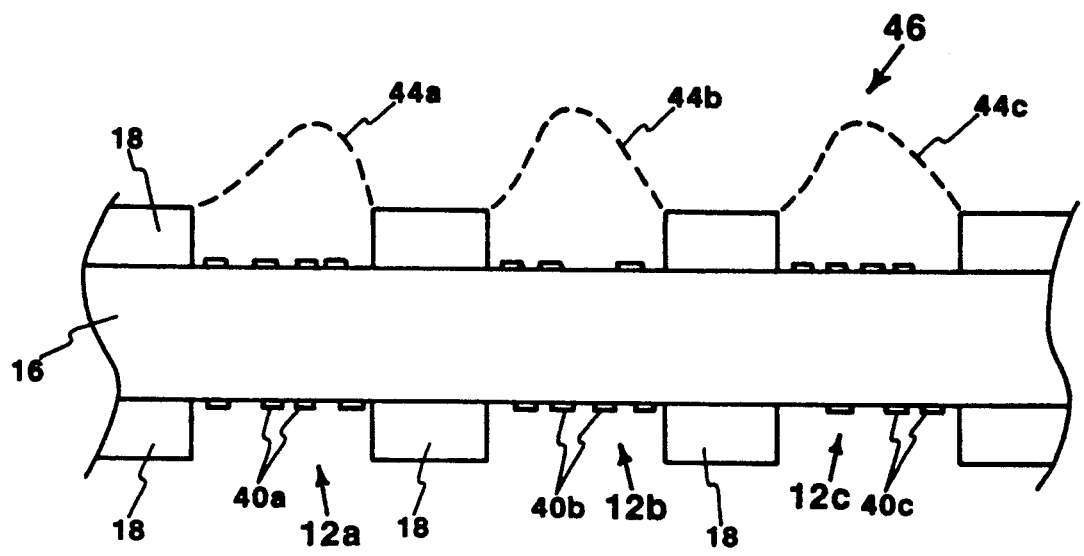
FIG. 3 is a cross-sectional view of a refractive index sensor with multiple sensing regions.
Figure 4:
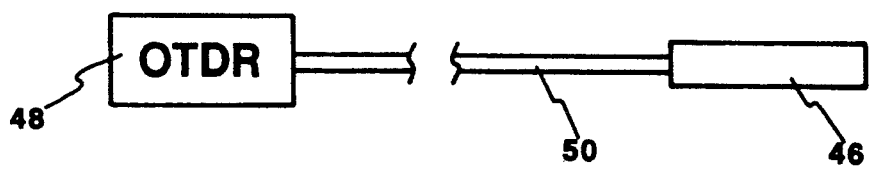
FIG. 4 is a diagram of a measurement system for a refractive index sensor with multiple sensing regions.

The design illustrated in FIG. 2 can be incorporated into a compound sensor 46 as shown in FIG. 3. A plurality of sensing regions 12a,b,c are formed on fiber core 16 in gaps between conventional clad 18. Each sensing region 12a,b,c has a respective discontinuous clad 40a,b,c which produces a leakage intensity profile 44a,b,c. The clads 40a,b,c could all be the same or they could be different, with particular specificities for different species, so that multiple species can be detected. The multiple sensor 46 can be used in combination with an optical time domain reflectometer (OTDR) 48, as shown in FIG. 4. Sensor 46 is connected to OTDR 48 through optical fiber 50. The OTDR 48 is used to identify the individual sensing regions 12a,b,c.

Although the invention has been described with respect to a fiber optic sensor, other waveguides such as a planar or channel waveguide can also be utilized.

Figure 5A:
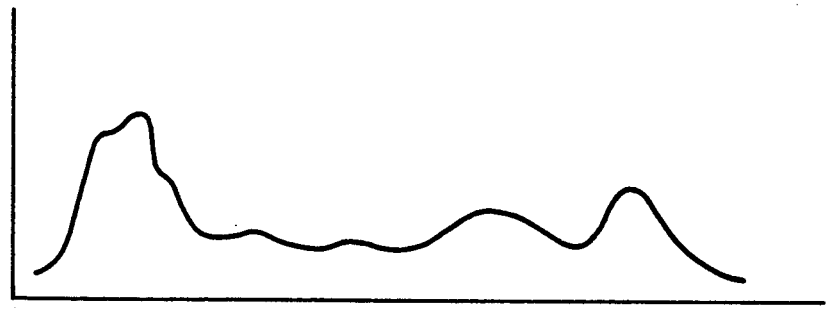
FIGS. 5A,B are plots of measured light leakage intensity along the length of a fiber optic.
Figure 5B:
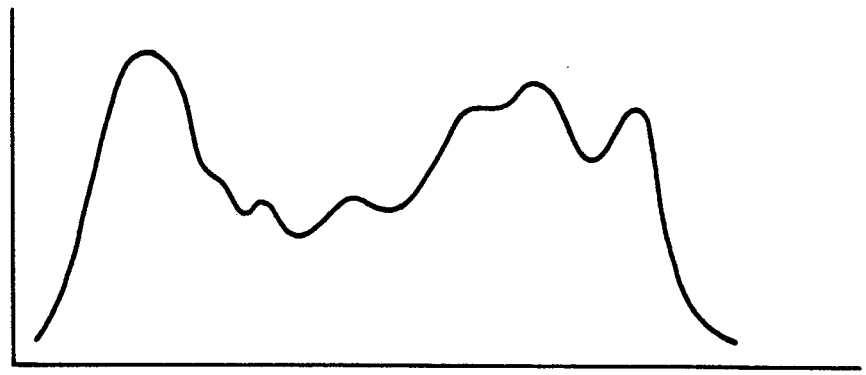

Measured light leakage intensity along the length of a fiber, verifying the principles of the invention, is shown in FIGS. 5A,B. In the plots, the fiber is oriented along the X-axis. In the fiber of FIG. 5A, the thin film metal clad is substantially uniform along the length of the sensing region. Therefore, the intensity profile shows a large peak at the beginning of the region and a smaller peak at the end, as expected, since these two points present the only substantial index discontinuities. In the fiber of FIG. 5B, the thin film metal clad is not uniform but has a number of index discontinuities due to nonuniformities in the clad along the length of the sensing region. The intensity profile, as expected, shows substantial light leakage along the length of the entire region, thus maximizing use of the sensing region and increasing sensor sensitivity.

Changes and modifications in the specifically described embodiments can be carried out without departing from the scope of the invention which is intended to be limited only by the scope of the appended claims.

We claim:

1. A refractive index optical sensor, comprising:
    light guiding means through which an optical beam propagates by total internal reflection;
    a thin film metal clad segment formed on the light guiding means, the metal clad segment having an effective thickness and light transmissivity which in combination with a surrounding medium produces a localized refractive index and a controlled leakage of light which modulates the transmission of light through the light guiding means as a function of the refractive index of the surrounding medium;
    the metal clad segment having a length such that light leakage occurs substantially along the entire length of the segment.

2. The sensor of claim 1 wherein the light guiding means is a fiber optic core.

3. The sensor of claim 1 wherein the light guiding means is a planar or channel waveguide.

4. The sensor of claim 1 wherein the metal clad segment has a length substantially equal to the length of the light guiding means along which a light beam propagating through the light guiding means by total internal reflection is first incident on the metal clad segment.

5. The sensor of claim 1 wherein the metal clad segment has a length substantially equal to the length of the leakage intensity profile through the metal clad segment.

6. The sensor of claim 1 further comprising a plurality of said thin film metal clad segments formed on the light guiding means in a spaced relationship, the spacing between segments being such that the leakage intensity profiles produced by each segment are sufficiently close to combine to form an aggregate intensity profile.

7. The sensor of claim 6 wherein the spacing between segments is regular.

8. The sensor of claim 6 wherein the spacing between segments is irregular.

9. A refractive index optical sensor, comprising:
    an optical fiber having a core and conventional clad;
    a sensing region formed on the optical fiber in a region where the conventional clad is removed;
    a discontinuous thin film metal clad formed in the sensing region, the metal clad producing a controlled leakage of light from the fiber core as a function of the refractive index of a surrounding medium, the discontinuous metal clad having a plurality of spaced segments, each segment having a length such that light leakage occurs substantially along the entire length of the segment.

10. The sensor of claim 9 wherein the metal clad segments are spaced to produce discontinuities in refractive index so that light leakage occurs substantially along the entire length of the sensing region.

11. The sensor of claim 9 wherein the metal clad segments are sufficiently close so that the leakage intensity profiles produced by each segment are sufficiently close to combine to form an aggregate intensity profile.

12. The sensor of claim 9 wherein the spacing between segments is regular.

13. The sensor of claim 9 wherein the spacing between segments is irregular.

14. The sensor of claim 9 further comprising a plurality of said sensing regions formed on the optical fiber.

15. The sensor of claim 14 wherein each sensing region is specific to a different species.

16. The sensor of claim 14 wherein all sensing regions are specific to the same species.

17. The sensor of claim 14 further comprising an optical time domain reflectometer optically connected to the sensor to identify individual sensing regions.

18. A refractive index optical sensor, comprising: light guiding means through which an optical beam propagates by total internal reflection;
- a plurality of sensing regions formed on the light guiding means;
- a discontinuous thin film metal clad formed in each sensing region, each metal clad producing a controlled leakage of light from the light guiding means as a function of the refractive index of a surrounding medium, each discontinuous metal clad having a plurality of spaced segments, each segment having a length such that light leakage occurs substantially over the entire length of the segment, the segments being spaced so that light leakage occurs substantially over the entire length of the sensing region.

19. The sensor of claim 18 wherein each sensing region has a metal clad which is specific to a different species.

20. The sensor of claim 18 wherein the light guiding means is a planar or channel waveguide.

* * * * *